United States Patent
Laqua et al.

(10) Patent No.: US 6,750,365 B2
(45) Date of Patent: Jun. 15, 2004

(54) THERMAL DISSOCIATION OF ALLOPHANATES

(75) Inventors: Gerhard Laqua, Kapellen (DE); Matthias Klötzer, Kroppen (DE); Volker Krase, Lauchhammer (DE); Peter Pfab, Schwarzheide (DE); Joachim Pfeffinger, Ludwigshafen (DE); Andreas Schmidt, Boxdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 89 days.

(21) Appl. No.: 10/133,329

(22) Filed: Apr. 29, 2002

(65) Prior Publication Data

US 2002/0161257 A1 Oct. 31, 2002

(30) Foreign Application Priority Data

Apr. 30, 2001 (DE) ......................... 101 21 282

(51) Int. Cl.$^7$ ............................ C07C 261/00
(52) U.S. Cl. ........................................ 560/157
(58) Field of Search .......................... 560/157

(56) References Cited

U.S. PATENT DOCUMENTS 3,392,184 A * 7/1968 Ulrich et al. ............... 558/233

OTHER PUBLICATIONS

Yoshitake et al, Poymer Degradation and Stability, vol. 18, (1987), pp 341–348.*
Yoshitake et al, Journal of Analytical Applied Pyrolysis, (1995) vol. 33 pp 269–281.*
Kogon et al, Journal of Organic Chemistry, (1958), vol. 23 p. 1594.*

* cited by examiner

*Primary Examiner*—Paul Killos
(74) *Attorney, Agent, or Firm*—Oblon, Spivak, McClelland, Maier & Neustadt, P.C.

(57) ABSTRACT

The present invention relates to a process for the dissociation of allophanates, in which a thermal dissociation is carried out in a reaction vessel and the gaseous dissociation products obtained are removed from the reaction vessel using an inert carrier gas or the vapor of a liquid as stripping medium and are condensed.

21 Claims, No Drawings

THERMAL DISSOCIATION OF ALLOPHANATES

The present invention relates to the thermal dissociation of chemical compounds, preferably allophanates, in particular compounds which bear a triply alkyl-substituted allophanate function as characteristic functional group (N,N',O-trialkyl allophanates).

N,N',O-trisubstituted allophanates formed by the addition of isocyanates onto urethane functions have been known for a long time and have been comprehensively described. They are frequently formed deliberately as crosslinking points in the production of polyurethanes or isocyanate-containing and isocyanate-capped prepolymers (e.g. in Houben/Weyl "Methoden der Organischen Chemie" in E. Muller Vol. XIV/2, Chapter III "Polyurethane" and D. Dieterich Vol. E20.2, Chapter II b y3) "Polyurethane"—Georg Thieme Verlag and D. Dieterich in "Ullmann's Encyclopedia of Industrial Chemistry" Vol. A21, Chapter "Polyurethanes"—VCH).

To determine the allophanate content of these polyurethanes or prepolymers, the allophanate groups have to be cleaved again. This allophanate cleavage can be carried out, for example, by aminolysis (cf., for example, D. Joel, G. Schulz, Plaste Kautsch., 32(4), 1985, 151–153; D. Joel, M. Weiler, Plaste Kautsch., 27(7), 1980, 374–376; M. Furukawa, T. Yokoyama, J. Polym. Sci.—Polym. Lett., 17, 1979, 175–180; I. G. Foliforowa, B. M. Bulgyin, L. I. Kopusov, Zavod. Lab., 41(6), 1975, 671–673).

Another method of determining the allophanate content is pyrolysis and subsequent chromatographic (GC) and/or spectroscopic analysis (IR, MS) of the dissociation products (cf., for example, N. Yoshitake, M. Furukawa, J. Anal. Appl. Pyrol., 33, 1995, 269–281; N. Yoshitake, N. Furukawa, T. Yokoyama, Polym. Degrad. and Stab, 29, 1990, 341–352 and 18, 1987, 341–348).

However, these studies relate exclusively to N,N'-diaryl-O-alkyl allophanates as model compounds for polyurethane materials and elastomers. The pyrolysis is carried out at from 250° C. to 550° C. Apart from aryl isocyanates and the alcohol component, additional dissociation products such as carbodiimides and carbon dioxide are also formed in the pyrolysis.

A base-catalyzed thermal dissociation of allophanates to liberate isocyanates is described in DE 30 40 692 A1. However, this method is restricted to the dissociation of N,N'-dialkyl-O-aryl allophanates and requires the presence of organic carbonates.

In the phosgene-free preparation of isocyanates by thermal dissociation of urethanes, there is often also undesirable formation of allophanates due to reaction of the urethanes used with the isocyanates liberated in the dissociation. These allophanates frequently form relatively nonvolatile bottom products, but can partly be converted back into the corresponding urethanes by alcoholysis in the presence of the corresponding 0-substituted carbamates at 240° C. This procedure is described, for example, in DE 196 28 552 A.

The preparation of carbamic esters by alcoholysis of the corresponding allophanates is also described, for example, in DE 33 27 824 A1.

Furthermore, U.S. Pat. No. 3,392,184 discloses the thermal dissociation of trialkyl allophanates to give isocyanates. However, a disadvantage of this method is that the dissociation products obtained are stripped out of the reaction mixture in insufficient yield.

It is an object of the present invention to provide a process for the thermal dissociation of allophanates which avoids the above-described disadvantages of the prior art and makes it possible, in particular, to obtain the dissociation products in improved yields.

We have found that this object is achieved by a process for the thermal dissociation of allophanates in a reaction vessel, in which the gaseous dissociation products obtained are removed from the reaction vessel using an inert carrier gas or the vapor of a liquid as stripping medium and are condensed.

According to the present invention, temperature and pressure in the reaction vessel are selected so that the desired dissociation products are obtained in gaseous form.

The thermal allophanate dissociation is preferably carried out at from 150° C. to 350° C., in particular from 180° C. to 280° C. The reaction is preferably carried out under atmospheric pressure, particularly preferably under subatmospheric pressure. The pressure is very particularly preferably 0.01–1 bar.

The thermal allophanate dissociation can, if desired, be accelerated by means of suitable catalysts. As suitable allophanate dissociation catalysts, preference is given to using inorganic or organic metal compounds (e.g. metal alkoxides, acetylacetonates, carboxylates, halides and pseudohalides) of groups IIIa, IVa, Ib, IIb, IVb, VIb, VIIb, VIIIb, in particular compounds of aluminum, tin, copper, zinc, titanium, zirconium, molybdenum, manganese, iron, copper and nickel.

To separate the allophanate dissociation products from the reaction mixture, use is made, according to the present invention, of suitable inert carrier gases and/or vapors of liquids, nitrogen, inert solvent vapors and/or alcohol vapors as stripping medium Preference is given to nitrogen, inert solvent vapors and alcohol vapors, very particularly preferably nitrogen.

According to the present invention, alkyl allophanates are preferably used as starting materials. The dissociation can be carried out using, in particular, the following compounds:

monoallophanates and/or polyallophanates derived from (cyclo)aliphatic monoisocyanates monoallophanates and/or polyallophanates which are derived from (cyclo)aliphatic polyisocyanates and contain isocyanate groups and/or carbamate groups monoallophanates and/or polyallophanates derived from (cyclo)aliphatic monoalcohols and/or polyalcohols.

Particular preference is given to using N,N',O-trialkyl allophanates.

The abovementioned alkyl allophanates can be dissociated on their own and/or in admixture with further allophanates and/or in admixture with high-boiling solvents which are nonvolatile and unreactive toward the dissociation products, in particular toward the isocyanates, under the chosen dissociation conditions.

It can be advisable, especially for the purpose of minimizing recombination and/or subsequent reactions (in particular allophanate and isocyanurate formation), to carry out the reaction in the presence of one or more high-boiling solvents, in particular solvents which are unreactive toward isocyanates.

As high-boiling solvents which are nonvolatile and unreactive toward isocyanates under the chosen dissociation conditions, it is possible to use, in particular, saturated long-chain linear and/or aromatic hydrocarbons, halogenated hydrocarbons and ethers. The solvents used are advantageously chosen so that the trialkyl allophanates used for the dissociation dissolve sufficiently in the respective solvent under the dissociation conditions selected.

It is also possible to deactivate reactive dissociation products, e.g. isocyanates, if necessary so as to prevent subsequent reactions. This can be achieved, for example, by chemical quenching (i.e. conversion into unreactive products) of the dissociation products, in particular the isocyanate, by means of suitable substances (e.g. monosubstituted or disubstituted amines, thiols, alcohols).

According to the present invention, preference is given to a process for obtaining isocyanate and urethane or isocyanate and alcohol by thermal dissociation of N,N',O-trialkyl allophanates. The substances mentioned can be formed by the following reactions:

Accordingly, a reaction carried out according to stage 1 can be employed for obtaining isocyanates and urethanes by thermal dissociation of the allophanates. Choice of the dissociation conditions (temperature and pressure) enables the allophanate dissociation to be stopped in a targeted manner at the first stage, viz. the formation of the corresponding N,O-dialkyl carbamates with elimination of the corresponding alkyl isocyanates.

Reaction temperature and pressure are preferably selected so that the dissociation products urethane and isocyanate are gaseous under the given conditions. Particular preference is given to reaction temperatures of 150–280° C., very particularly preferably 180–260° C.

The reaction is preferably carried out at a pressure of 0.01–1 bar, but particular preference is given to a pressure of 0.01–0.2 bar.

It is also possible to obtain isocyanates and alcohols by thermal dissociation of the allophanates according to stage 2. In this case, reaction temperature and pressure are chosen so that isocyanates and alcohol are obtained in gaseous form. The temperatures are preferably 180–350° C., particularly preferably 220–300° C.

Preference is given to carrying out the reaction at a pressure of 0.01–1 bar. Particular preference is given to a pressure of 0.02–1 bar, most preferably 0.04–1 bar.

The pyrolysis intermediate urethane remains in the reaction vessel and is dissociated further into isocyanates and alcohol.

Urethane dissociation product from stage 1 which has become entrained in the gaseous dissociation products can, if desired, be separated off by use of suitable separation apparatuses (e.g. packed columns or rectification columns) and returned as runback to the reaction vessel.

The invention is illustrated by the examples below:

EXAMPLE 1

In a suitable reaction vessel, a mixture of 100 g of octadecane and 30 g of N,N',O-tri-n-butyl allophanate (0.1103 mol) was quickly heated to 240° C. in the presence of 30 ppm of iron (in the form of iron (III) acetylacetonate) under atmospheric pressure while stirring vigorously and while passing a continuous stream of 100 ml/min of nitrogen through the vessel, and the mixture was maintained at this temperature The volatile compounds obtained were condensed in a Liebig condenser and collected in a defined excess of a toluene solution of di-n-butylamine. After prompt formation of condensate at the beginning, this steadily decreased, so that the allophanate dissociation was stopped after 20 minutes. GC analysis of the quench solution gave the following result:

butyl isocyanate (in the form of 22.3 g of N,N,N'-tributylurea)=0.0978 mol (which corresponds to a yield of 88.7% based on tributyl allophanate in dissociation stage 1)

10.6 g of N,O-dibutyl carbamate=0.0613 mol (which corresponds to a yield of 55.6% based on tributyl allophanate)

According to gas chromatography, the reaction residue comprised unreacted tributyl allophanate and a further 4.82 g of N,O-dibutyl carbamate (0.0279 mol; 25.3% based on tributyl allophanate).

EXAMPLE 2

In a suitable reaction vessel, a mixture of 100 g of octadecane and 30.15 g of N,N',O-tri-n-butyl allophanate (0.11085 mol) was quickly heated to 259° C. under atmospheric pressure while stirring vigorously and while passing a continuous stream of 10 ml/min of nitrogen through the vessel, and the mixture was maintained at this temperature.

The volatile compounds obtained were condensed in a Liebig condenser and collected in a defined excess of a toluene solution of di-n-butylamine. After prompt formation of condensate at the beginning, this steadily decreased, so that the allophanate dissociation was stopped after 8 minutes. GC analysis of the quench solution gave the following result:

butyl isocyanate (in the form of 22.1 g of N,N,N'-tributylurea)=0.09706 mol (which corresponds to a yield of 87.6% based on tributyl allophanate in dissociation stage 1)

14.1 g of N,O-dibutyl carbamate=0.0815 mol (which corresponds to a yield of 73.5% based on tributyl allophanate)

0.08 g of butanol=0.0011 mol (which corresponds to a yield of 1.0% based on tributyl allophanate)

According to gas chromatography, the reaction residue comprised unreacted tributyl allophanate and a further 2.05 g of N,O-dibutyl carbamate (0.01185 mol; 10.7% based on tributyl allophanate).

COMPARATIVE EXAMPLE

In a suitable reaction vessel provided with a superposed packed column, a mixture of 50 g of octadecane and 60.3 g of N,N',O-tri-n-butyl allophanate (0.2217 mol) was quickly heated to 225° C. in the presence of 30 ppm of iron (in the form of iron (III) acetylacetonate) under atmospheric pressure while stirring vigorously and was maintained at this temperature.

The volatile compounds obtained were condensed in a Liebig condenser and collected in a defined excess of a toluene solution of di-n-butylamine. After initially low formation of condensate at the beginning, this gradually increased, remained constant for a while and then decreased again so that the allophanate dissociation was stopped after 120 minutes. GC analysis of the quench solution gave the following result:

butyl isocyanate (in the form of 81.9 g of N,N,N'-tributylurea)≅0.35915 mol (which corresponds to a yield of 81.0% based on tributyl allophanate in dissociation stage 2)

0.18 g of N,O-dibutyl carbamate≅0.00104 mol (which corresponds to a yield of 0.47% based on tributyl allophanate)

15.09 g of butanol 0.2039 mol (which corresponds to a yield of 92.0% based on tributyl allophanate)

According to gas chromatography, the reaction residue comprised unreacted tributyl allophanate and a further 3.98 g of N,O-dibutyl carbamate (0.023 mol; 10.4% based on tributyl allophanate).

This comparative example makes it clear that the use of carrier gas has a decisive influence on the nature of the reaction products. In particular, it is found that the yields in the examples according to the invention are higher than in the comparative example.

What is claimed is:

1. A process comprising removing gaseous dissociation products obtained from thermal dissociation of allophanates, from a reaction vessel using an inert carrier gas or the vapor of a liquid as stripping medium, and condensing said gaseous dissociation products.

2. The process as claimed in claim 1, wherein the inert carrier gas or vapor of a liquid is nitrogen, the vapor of an inert solvent or an alcohol vapor or a mixture thereof.

3. The process as claimed in claim 1, wherein the allophanates are trialkyl allophanates.

4. The process as claimed in claim 1, wherein temperature and pressure are set so that the desired dissociation products are obtained in gaseous form.

5. The process as claimed in claim 4, wherein the temperature is set to from 150° C. to 350° C.

6. The process as claimed in claim 5, wherein the temperature is set to from 180° C. to 280° C.

7. The process as claimed in claim 4, wherein the thermal dissociation is carried out under atmospheric pressure.

8. The process as claimed in claim 4, wherein the thermal dissociation is carried out under subatmospheric pressure.

9. The process as claimed in claim 4, wherein the pressure is 0.01–1 bar.

10. The process as claimed in claim 4, wherein temperature and pressure are chosen so that the dissociation products urethane and isocyanate are obtained in gaseous form.

11. The process as claimed in claim 10, wherein the temperature is set to 150–280° C.

12. The process as claimed in claim 11, wherein the temperature is set to 180–260° C.

13. The process as claimed in claim 10, wherein the dissociation is carried out at a pressure of 0.01–1 bar.

14. The process as claimed in claim 13, wherein the dissociation is carried out at a pressure of 0.01–0.2 bar.

15. The process as claimed in claim 4, wherein pressure and temperature are chosen so that the dissociation products isocyanate and alcohol obtained are in gaseous form.

16. The process as claimed in claim 15, wherein the temperature is set to 180–350° C.

17. The process as claimed in claim 16, wherein the temperature is set to 220–300° C.

18. The process as claimed in claim 15, wherein the dissociation is carried out at a pressure of 0.02–1 bar.

19. The process as claimed in claim 18, wherein the pressure is set to 0.04–1 bar.

20. The process as claimed in claim 1, wherein the thermal dissociation is carried out in the presence of catalysts.

21. The process as claimed in claim 20, wherein inorganic or organic metal compounds are used as catalysts.

* * * * *